(12) United States Patent
Gao et al.

(10) Patent No.: US 11,865,129 B2
(45) Date of Patent: Jan. 9, 2024

(54) APPLICATION OF ANEMOSIDE B4 IN PREPARATION OF A DRUG FOR TREATMENT OR PREVENTION OF PSORIASIS

(71) Applicant: GUANGXI XINHAI PHARMACEUTICAL TECHNOLOGY CO., LTD., Liuzhou (CN)

(72) Inventors: Hongwei Gao, Suzhou (CN); Shilin Yang, Suzhou (CN); Renyikun Yuan, Suzhou (CN); Xiaoran Li, Suzhou (CN)

(73) Assignee: GUANGXI XINHAI PHARMACEUTICAL TECHNOLOGY CO., LTD., Liuzhou (CN)

( * ) Notice: Subject to any disclaimer, the term of this patent is extended or adjusted under 35 U.S.C. 154(b) by 0 days.

(21) Appl. No.: 17/805,217

(22) Filed: Jun. 2, 2022

(65) Prior Publication Data
US 2023/0201230 A1    Jun. 29, 2023

(30) Foreign Application Priority Data
Dec. 24, 2021 (CN) .......................... 202111601109.7

(51) Int. Cl.
| | | |
|---|---|---|
| A61K 31/704 | (2006.01) | |
| A61P 17/06 | (2006.01) | |
| A61K 9/00 | (2006.01) | |

(52) U.S. Cl.
CPC .......... A61K 31/704 (2013.01); A61K 9/0014 (2013.01); A61P 17/06 (2018.01)

(58) Field of Classification Search
None
See application file for complete search history.

(56) References Cited

U.S. PATENT DOCUMENTS 11,510,933 B2 * 11/2022 Yang ........................ A61P 31/04

FOREIGN PATENT DOCUMENTS

EP        3747446 A1 * 12/2020 ............. A61K 31/35

* cited by examiner

*Primary Examiner* — Traviss C McIntosh, III
(74) *Attorney, Agent, or Firm* — CBM PATENT CONSULTING, LLC

(57) ABSTRACT

The present disclosure relates to an application of anemoside B4 in preparation of drug for treatment or prevention of psoriasis. Anemoside B4 has therapeutic effect on 5% imiquimod-induced psoriatic lesions in mice. Its possible mechanism may be inhibiting inflammation reactions, regulating immune function and inhibiting angiogenesis, and the therapeutic effect may be realized by inhibiting the release of IL-12, IL-17, IL-6 and IL-1β in skin tissue. This study of the present disclosure laid a theoretical foundation for the subsequent development of anemoside B4 into an anti-psoriasis drug of traditional Chinese medicine.

6 Claims, 5 Drawing Sheets

APPLICATION OF ANEMOSIDE B4 IN PREPARATION OF A DRUG FOR TREATMENT OR PREVENTION OF PSORIASIS

TECHNICAL FIELD

The present disclosure relates to the technical field of drugs. More specifically, the present disclosure relates to an application of anemoside B4 in preparation of a drug for treatment or prevention of psoriasis.

BACKGROUND

Psoriasis is a common chronic inflammatory disease in clinic, which has a mainly clinical manifestation of extensively scaly erythema on the trunk and extremities, and is characterized by difficult treatment and easy reappearance. The incidence rate of psoriasis in China is 0.47%. Psoriasis vulgaris is the most common type of psoriasis, which has complex pathogenesis, and is considered to be related to many factors, such as heredity, inflammation, mental stress, drugs, immune disorders and so on. Biological preparations have developed rapidly in recent years, which is greatly helpful for the treatment of psoriasis. However, the biological preparations are expensive and may have unintended side effects. Currently, local treatment can be used for patients with slight partly psoriasis, and phototherapy or systemic drugs can be used for patients with moderate or severe psoriasis. The western medical treatment of psoriasis mainly adopts glucocorticoid for external use, which has limited effect, and causes the cuticle of the skin to become thinner because of long-time external use of glucocorticoid. Therefore, safety, effectiveness, stability and economy have become the core issues in the treatment of psoriasis. The traditional Chinese medicine treatment of psoriasis has become a research hotspot. Blood-heat syndrome is the most common clinical form of psoriasis in the traditional Chinese medicine, so that nutrient and blood of body are lost, blood heat is accumulated, dryness-transmission and wind-engendering, and skin dystrophy are formed. *Pulsatilla chinensis* (Bge.) Regel has effects of heat-eliminating and detoxication, and blood-cooling. Currently, no studies had been conducted with anemoside B4 for treatment or prevention of psoriasis.

SUMMARY

An object of the present disclosure is to provide an application of anemoside B4 in preparation of a drug for treatment or prevention of psoriasis. Anemoside B4 has treatment effect on psoriasis, its mechanism may be related to inhibiting inflammation reactions, regulating immune function, and inhibiting angiogenesis.

In order to achieve these objects and other advantages according to the present disclosure, an application of anemoside B4 in preparation of drugs for treatment or prevention of psoriasis is provided, wherein, anemoside B4 has the structural formula of (I):

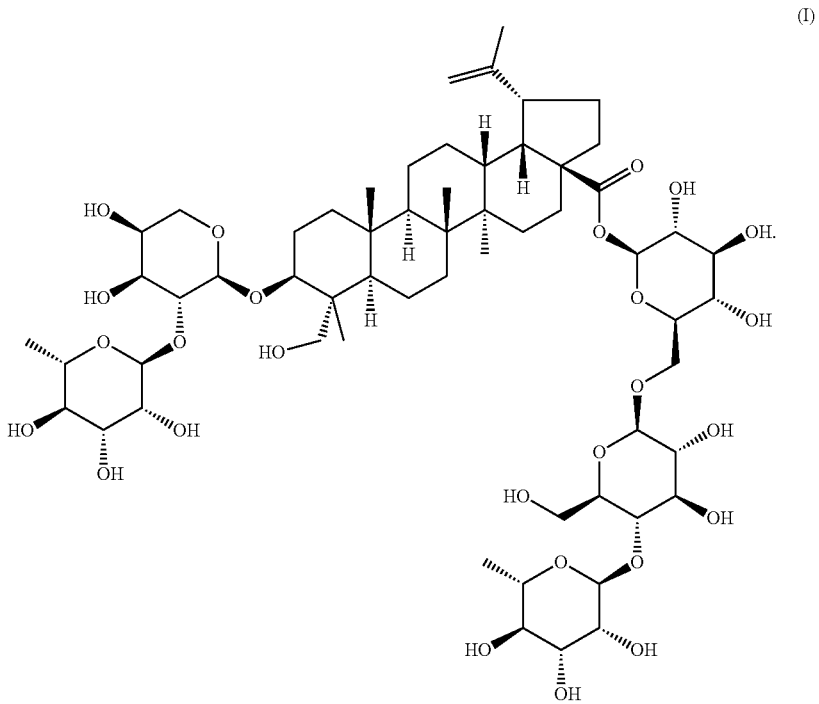

Preferably, the drug includes anemoside B4 with a therapeutic effective dosage and a pharmaceutically acceptable carrier.

Preferably, the drug includes hydrochloride, perchlorate, methanesulfonate, phosphate, citrate or sulfate of anemoside B4 with the therapeutic effective dosage, and the pharmaceutically acceptable carrier.

Preferably, the pharmaceutically acceptable carriers include a diluent, a solubilizer, a cosolvent, a disintegrant, a dispersant, a lubricant, a corrective agent, an antioxidant, a binder, an absorbent, a wetting agent, a buffer and a cross-linking agent.

Preferably, the drug is formed into pharmaceutically permissible preparations.

Preferably, the preparations include pills, tablets, powders, capsules, granules, dripping pills, drops, sprays, injections, suspensions, creams, gels and suppositories.

Preferably, the preparation is creams.

Preferably, the cream is prepared by mixing stearic acid, glyceryl monostearate and castor oil, heating it to 70-85° C. in a water bath, stirring it to be completely melted to obtain an oil phase, mixing glycerin, anemoside B4 and distilled water, heating it to 70-85° C. in the water bath, adding triethanolamine under stirring until anemoside B4 is completely dissolved to obtain a water phase, adding the oil phase into the water phase under continuous stirring, and clockwise stirring it to 22-28° C.; wherein the total weight parts of stearic acid, glyceryl monostearate, castor oil, glycerin, anemoside B4 and distilled water are 100.

Preferably, a dosage of the anemoside B4 cream is not less than 1 mg/kg·d.

Preferably, a dosage of anemoside B4 is not less than 1 mg/kg·d.

The present disclosure at least includes the following advantageous effects:

Anemoside B4 has certain treatment effect on psoriasis, and has therapeutic effect on 5% imiquimod-induced psoriatic lesions in mice. Its possible mechanism may be inhibiting inflammation reactions, regulating immune function and inhibiting angiogenesis, and the therapeutic effect may be realized by inhibiting the release of IL-12, IL-17, IL-6 and IL-1β in skin tissue. This study of the present disclosure laid a theoretical foundation for the subsequent development of anemoside B4 into an anti-psoriasis drug of the traditional Chinese medicine.

Other advantages, objects and features of the present disclosure will be partially reflected by the following description, and will be partially understood by those skilled in the art through researching and practicing the present disclosure.

DETAILED DESCRIPTION

Figure 1:
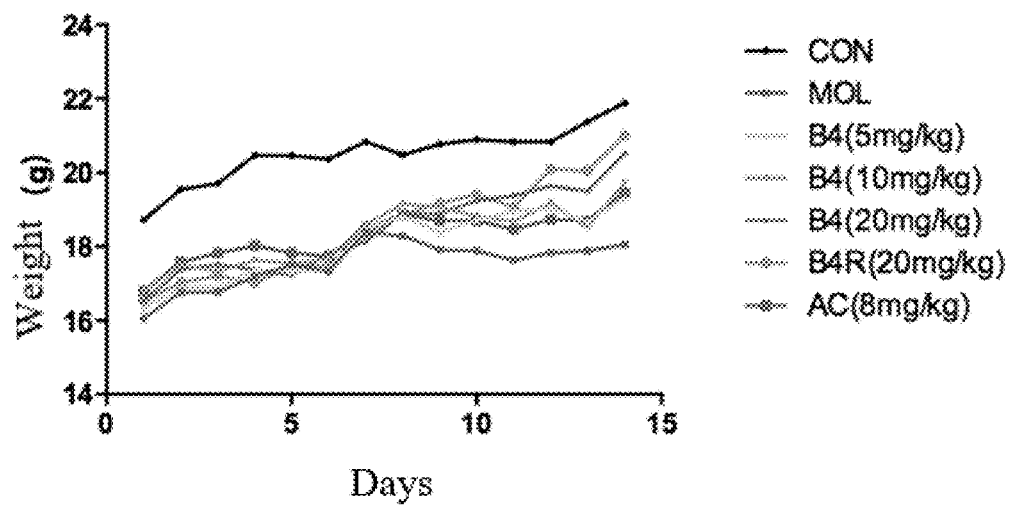
FIG. 1 is a diagram for showing the effect of anemoside B4 on weights of mice in a first animal group.

The present disclosure will be further described in detail hereinafter with reference to the accompanying drawings, so that those skilled in the art can implement the present disclosure with reference to the specification.

It should be noted that terms such as "having", "including" and "comprising" as used herein do not exclude presence or addition of one or more other elements or combinations thereof.

It should be noted that the experimental methods described in the following embodiments are all conventional methods unless otherwise specified, and the reagents and materials are commercially available unless otherwise specified.

an application of anemoside B4 in preparation of drugs for treatment or prevention of psoriasis is provided, wherein, anemoside B4 has the structural formula of (I):

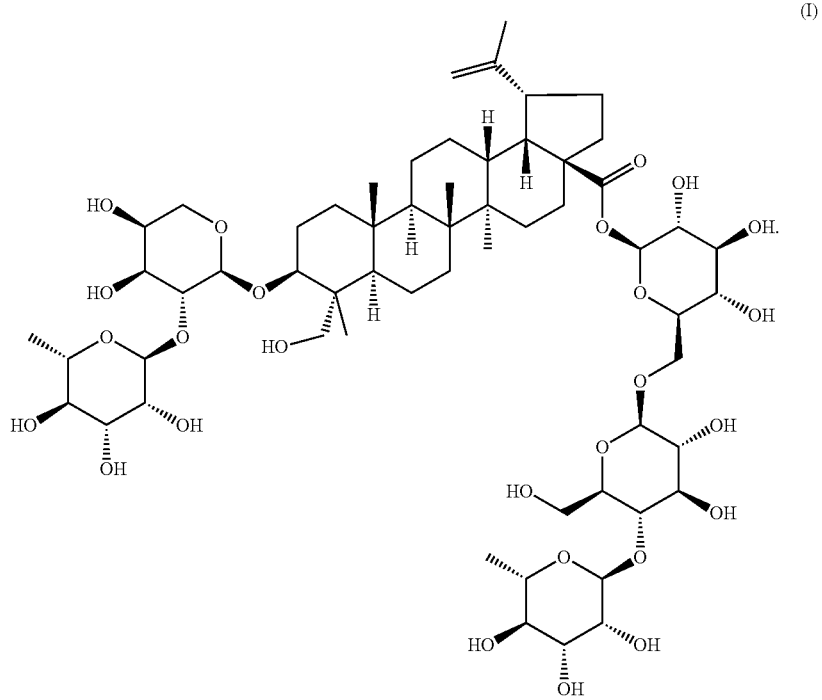

The drug includes anemoside B4 with a therapeutic effective dosage and a pharmaceutically acceptable carrier.

The drug includes hydrochloride, perchlorate, methanesulfonate, phosphate, citrate or sulfate of anemoside B4 with the therapeutic effective dosage, and the pharmaceutically acceptable carrier.

The pharmaceutically acceptable carriers include a diluent, a solubilizer, a cosolvent, a disintegrant, a dispersant, a lubricant, a corrective agent, an antioxidant, a binder, an absorbent, a wetting agent, a buffer and a crosslinking agent.

The drug is formed into pharmaceutically permissible preparations.

The preparations include pills, tablets, powders, capsules, granules, dripping pills, drops, sprays, injections, suspensions, creams, gels and suppositories.

The preparation is creams, which has better therapeutic effect.

The cream is prepared by mixing stearic acid, glyceryl monostearate and castor oil, heating it to 70-85° C. in a water bath, stirring it to be completely melted to obtain an oil phase, mixing glycerin, anemoside B4 and distilled water, heating it to 70-85° C. in the water bath, adding triethanolamine under stirring until anemoside B4 is completely dissolved to obtain a water phase, adding the oil phase into the water phase under continuous stirring, and clockwise stirring it to 22-28° C.

A dosage of the anemoside B4 cream is not less than 1 mg/kg d. A pharmaceutical preparation of the present disclosure is used in the form of dosage per body weight.

A dosage of anemoside B4 is not less than 1 mg/kg·d. The pharmaceutical preparation of the present disclosure is used in the form of dosage per body weight.

1. Materials and Methods 1.1. Medicines and Reagents

Anemoside B4 (extracted in the laboratory, the purity is greater than 98%), 5% imiquimod cream (batch number 101112, 40210904, Sichuan MED-SHINE Pharmaceutical Co., Ltd), Acitretin capsule (Medicine H 20010126, Chongqing Huapont Pharm Co., Ltd.), normal saline for injection (batch number L219012211, H21082605, Sichuan Kelun Pharmaceutical Co., Ltd.), IL-6, IL-1β, and IL-12 ELISA kits (batch number 269392-006, 261332-012, 245054-001, Thermo Fisher Scientific Inc.), IL-17 ELISA kits (batch number 202112, ELISA Biotechnology Co., Ltd), CD3, CD4 and CD8 antibodies purchased from BD corporation.

1.2. Experimental Animals

A first animal group: 56 SPF-grade BALB/c male mice (8 weeks old), weighing about 18-22 g.

A second animal group: 60 SPF-grade SD male rats (8 weeks old), weighing about 180 g.

The animals in the first animal group and the second animal group are purchased from Beijing Vital River Laboratory Animal Technology Co., Ltd., the animal certificate No. is SCXK Jing 2016-0006, all animals are raised in a SPF environment with the temperature of 18-24° C. and the humidity of 40%-50%, and the animals eat and drink freely, and the circadian rhythm is normal during the experiment period.

1.3. Instruments

A Mindray blood routine tester (Model: BC-5000vet, Shenzhen Mindray Biomedical Electronics Co., Ltd), a 1/1000 precise balance (Model ME204E, Mettler-Toledo Instrument Shanghai Co., Ltd.), a low-temperature high-speed centrifuge (Model 5425R, Eppendorf corporation), a pathological image analyzer (Model BX-60, Japan OLYMPUS), a microplate reader (Model Synergy H1, BioTek Instrumentes), and a tissue grinder (Model TP-24, Gering Instrument manufacturing Tianjin Co., Ltd).

1.4. Preparation of Anemoside B4 Cream 2.4 g stearic acid, 0.8 g glyceryl monostearate and 4.0 g castor oil are placed in a dry beaker, heated to 80° C. in a water bath, and stirred to be completely melted to obtain an oil phase. 2.0 g glycerin, 0.13 g anemoside B4 and 10 mL distilled water are placed in another beaker, heated to 80° C. in the water bath, and added triethanolamine under stirring until anemoside B4 is completely dissolved to obtain a water phase. The oil phase is added into the water phase under continuous stirring, and clockwise stirred to room temperature (24° C.).

1.5. Experimental Methods 1.5.1. Psoriasis Model Establishment and Administration of the First Animal Group:

56 SPF-grade BALB/c male mice in the first animal group are divided into 7 groups: a blank control group, a model control group, an anemoside B4 intragastric administration group (5 mg/kg), an anemoside B4 intragastric administration group (10 mg/kg), an anemoside B4 intragastric administration group (20 mg/kg), an acitretin capsules (AC) intragastric administration group (8 mg/kg), and an anemoside B4 cream group (20 mg/kg), and are respectively expressed into con, mol, B4-L, B4-M, B4-H, AC and B4-R in FIGS. 1, 2, 6, 7 and 8 for convenience. A shaving area on the back of the mice in each group is 2.5 cm×3 cm, and the vellus is removed with mild depilatory cream. The mice of each group except the blank control group are modeled by administrating 62.5 mg 5% imiquimod cream on the shaving area until the skin is thickened and has erythema and silver scales for modeling completely.

During the model establishment, 5% imiquimod cream is administrated once a day, and continuously administrated for 14 days. On the third day, the model establishment is continued and drugs are administered at the same time, wherein the mice in the AC intragastric administration group (8 mg/kg), the anemoside B4 intragastric (i.g.) administration group (5 mg/kg), the anemoside B4 intragastric administration group (10 mg/kg), and the anemoside B4 intragastric administration group (20 mg/kg) are administrated once a day, and continuously administrated for 12 days. The mice in the anemoside B4 cream group (20 mg/kg) are applied 62.5 mg anemoside B4 cream to the skin lesions once a day, and continuously applied for 12 days. The mice in the blank control group and the model control group are applied 62.5 mg Vaseline to the skin lesions once a day, and continuously applied for 12 days. The weight of the mice is recorded for counting the weight change of the mice.

Figure 3:
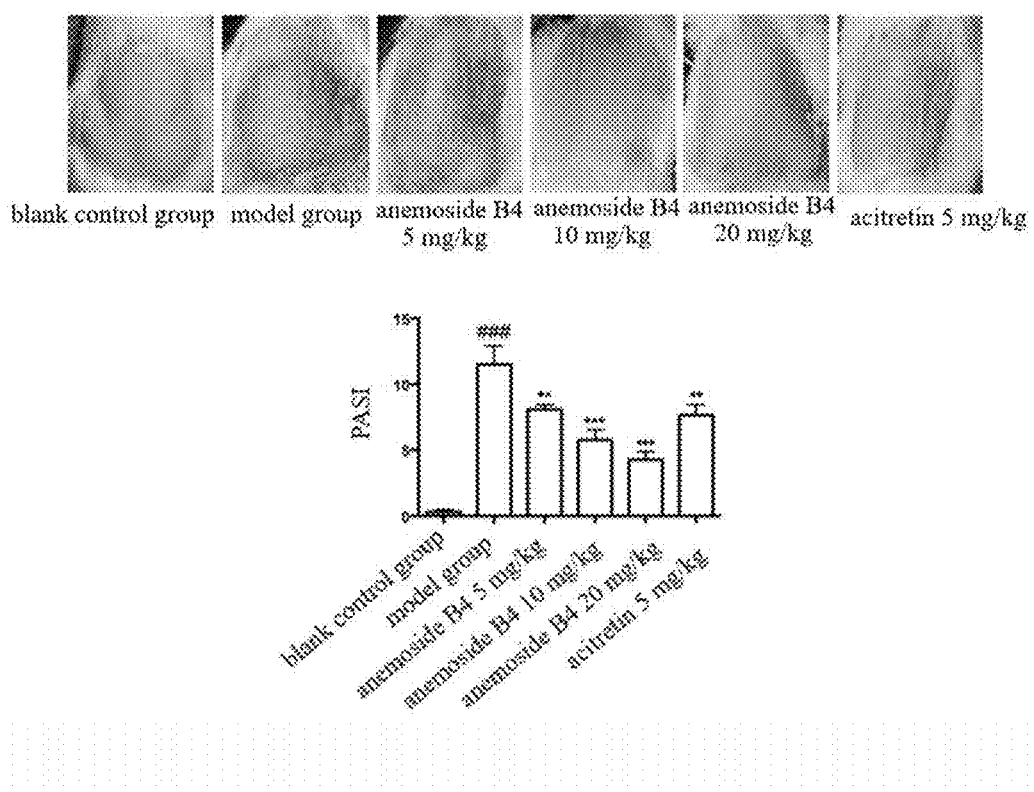
FIG. 3 is a diagram for showing the effect of anemoside B4 on psoriatic lesions and PASI of rats in a second animal group.
Figure 4:
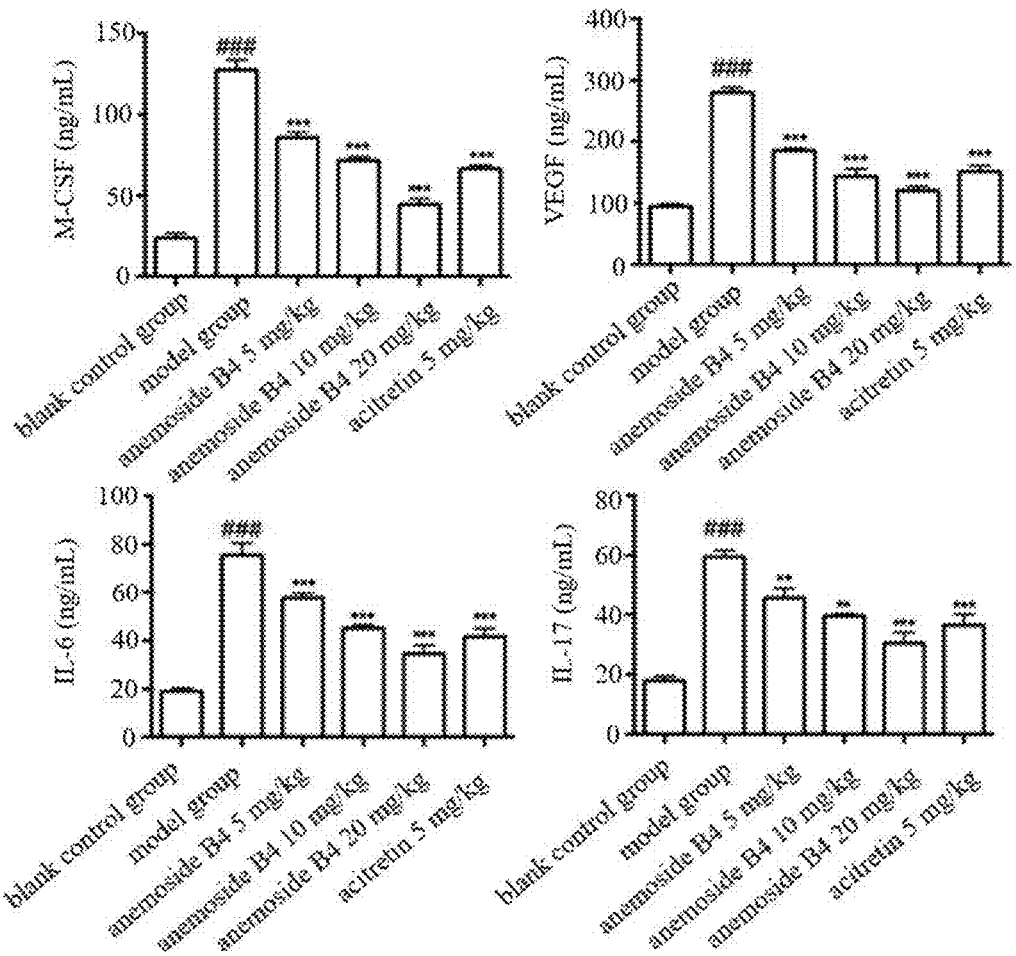
FIG. 4 is a diagram for showing the effect of anemoside B4 on M-CSF, VEGF, IL-6 and IL-17 level in serum of the rats in the second animal group.
Figure 5:
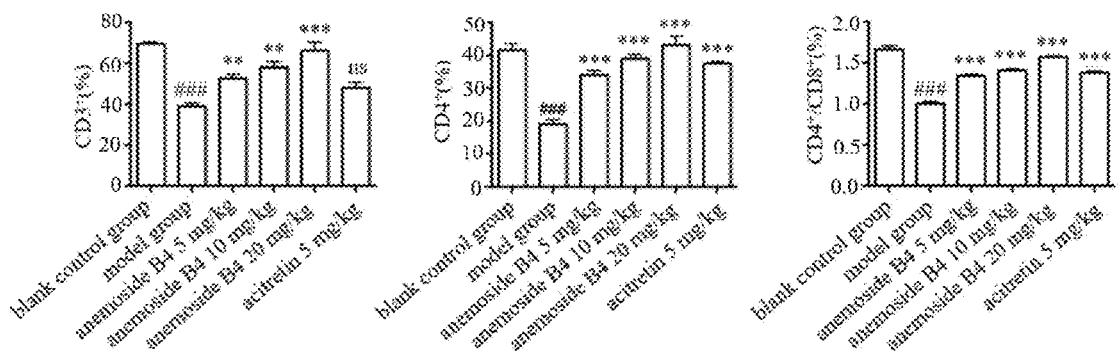
FIG. 5 is a diagram for showing the effect of anemoside B4 on T lymphocyte subsets of $CD4^+$, $CD3^+$, $CD4^+/CD8^+$ of the rats in the second animal group.

1.5.2. Psoriasis Model Establishment and Administration of the Second Animal Group:

60 SPF-grade SD male rats in the second animal group are divided into 6 groups: a blank control group, a model control group, an anemoside B4 intragastric administration group (5 mg/kg), an anemoside B4 intragastric administration group (10 mg/kg), an anemoside B4 intragastric administration group (20 mg/kg), and an acitretin intragastric administration group (5 mg/kg), and are respectively expressed into the blank control group, the model group, anemoside B4 5 mg/kg, anemoside B4 10 mg/kg, anemoside B4 20 mg/kg, and acitretin 5 mg/kg in FIGS. 3, 4 and 5 for convenience. A shaving area on the back of the rats in each group is 2.5 cm×3 cm, and the vellus is removed with mild depilatory cream. The rats of each group except the blank control group are modeled by administrating 62.5 mg 5% imiquimod cream on the shaving area until the skin is thickened and has erythema and silver scales for modeling completely.

5% imiquimod cream is administrated once a day, and continuously administrated for 8 days for model establishment. On the second day, the rats in each group are continuously intragastric (i.g.) administered drugs for 7 days.

2. Measurement of Indexes 2.1. PASI

The psoriasis area and severity index (PASI) of the mice in the first animal group and the rats in the second animal group is performed by taking photographs of the shaving area, giving 0-4 scores for the degree of erythema, scales and infiltration thickness in the skin lesions according to a PASI standard, and obtaining the total scores by summing the scores of the three parts; wherein the PASI standard is as follows: none 0, mild 1, moderate 2, severe 3, and extremely severe 4.

2.2. Measurement of M-CSF, VEGF, IL-6 and IL-17 Level in Serum by ELISA

After administration, blood is taken from abdominal aorta of the rats in each group of the second animal group, centrifuged to collect the serum, and measured the M-CSF, VEGF, IL-6 and IL-17 level in the serum by ELISA kits according to the procedures of specification.

2.3 Measurement of T Lymphocyte Subsets of $CD4^+$, $CD3^+$, $CD4^+/CD8^+$ in Serum by Flow Cytometry.

After administration, blood is taken from abdominal aorta of the rats in each group of the second animal group, added erythrocyte lysis buffer, centrifuged to collect T lymphocytes, incubated CD4, CD3 and CD8 antibodies in 4° C., washed with a buffer, centrifuged to collect cells, and is subjected to flow cytometry to measure the ratio of the T lymphocyte subsets.

2.4. Blood Analysis

Eyeball blood of the mice in each group of the first animal group is drawn on the last day, and measured the level of white blood cell (WBC), Neutrophilicgranulocyte (Neu) and Lymphocyte (Lym) in blood with the blood routine tester.

2.5. Comparison of the Spleen Coefficient

After blood collection of the mice in each group of the first animal group, the mice are killed by dislocation of cervical vertebra, quickly separated the spleen and weighed to obtain the wet weight of the spleen, recording and calculating the spleen coefficient, wherein the spleen coefficient (%)=(spleen wet weight/body weight)×100%.

2.6. Histopathological Observation

After blood collection of the mice in each group of the first animal group, the mice are killed by dislocation of cervical vertebra, separated the skin in the skin lesions, and removed subcutaneous fat. Taking a part, fixing it with 4% paraformaldehyde, embedding, obtaining section, dying with hematoxylin and eosin (HE), and observing histopathological changes of the skin under a light microscope.

2.7. Measurement of IL-12, IL-17, IL-6 and IL-1β Level in Skin Tissue 100 mg skin tissue of the mice in each group of the first animal group are precisely weighed, added 0.9 mL ice normal saline, homogenized with the tissue grinder, and centrifuged at 4° C. and 3000 rpm for 10 min. The supernatant is collected, and IL-12, IL-17, IL-6 and IL-1β level in the skin tissue are measured by kits according to the procedures of specification.

2.8. Statistical Analysis

The significant difference between groups is evaluated by ANOVA using Graphpad Prism software statistics, wherein P is less than 0.05 indicates there are significant events.

3. Experimental Results 3.1. The Effect of Anemoside B4 on Weights

In the first animal group, compared with the blank control group, the weights of the mice in the model control group, the anemoside B4 intragastric administration group (B4-L, 5 mg/kg), the anemoside B4 intragastric administration group (B4-M, 10 mg/kg), the anemoside B4 intragastric administration group (B4-H, 20 mg/kg), the acitretin capsules (AC) intragastric administration group (8 mg/kg), and the anemoside B4 cream group (B4-R, 20 mg/kg) are significantly decreased. compared with the model control group, the weight loss of the mice caused by psoriasis in the anemoside B4 intragastric administration group (5 mg/kg), the anemoside B4 intragastric administration group (10 mg/kg), the anemoside B4 intragastric administration group (20 mg/kg), the acitretin capsules (AC) intragastric administration group (8 mg/kg), and the anemoside B4 cream group (20 mg/kg) can be improved, and the improvement effect of the anemoside B4 cream group (20 mg/kg) is the best, as shown in FIG. 1, n=6, $^{\#\#\#}$p is less than 0.001, *p is less than 0.05, p is less than 0.01, *p is less than 0.001.

3.2. The Effect of Anemoside B4 on Psoriatic Lesions

Figure 2:
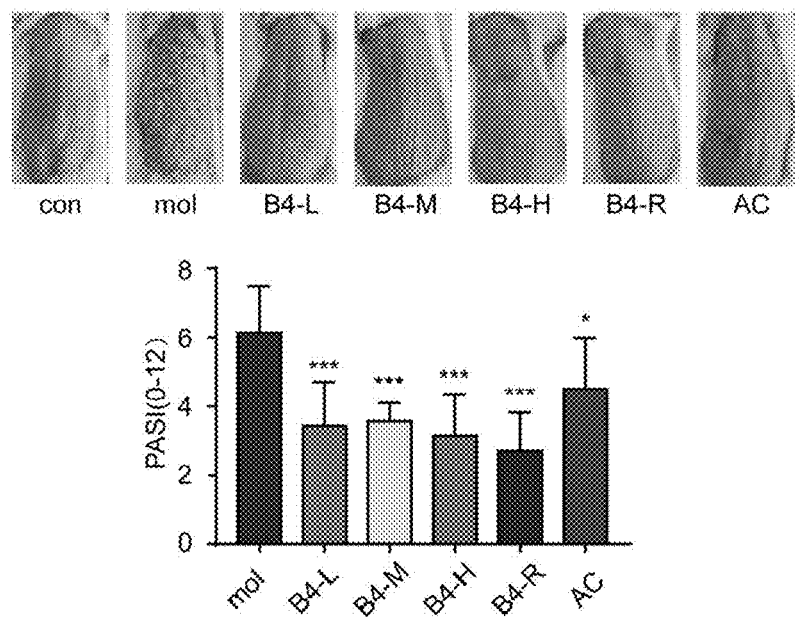
FIG. 2 is a diagram for showing the effect of anemoside B4 on psoriatic lesions and PASI of the mice in the first animal group.

In the first animal group, the mice in the blank control group have smooth skin and no psoriasis-like lesions, the mice in the model control group have thickened and uplifted skin, and typical characteristics of psoriasis with erythema and layered scales; and the skin lesions of the mice in the anemoside B4 intragastric administration group (B4-L, 5 mg/kg), the anemoside B4 intragastric administration group (B4-M, 10 mg/kg), the anemoside B4 intragastric administration group (B4-H, 20 mg/kg), the acitretin capsules (AC) intragastric administration group (8 mg/kg), and the anemoside B4 cream group (B4-R, 20 mg/kg) are significantly improved, wherein the erythema are subsided, thickened and uplifted skin is improved, and the scales are desquamated. The mice in the model control group have severe skin lesions and an average value of PASI reaches 6. The skin lesions of the mice in the anemoside B4 intragastric administration group (5 mg/kg), the anemoside B4 intragastric administration group (10 mg/kg), the anemoside B4 intragastric administration group (20 mg/kg), and the anemoside B4 cream group (20 mg/kg) are significantly improved, and the average value of PASI is decreased to 3 or below 3. The average value of PASI of the acitretin capsules (AC) intragastric administration group (8 mg/kg) is decreased to 5 or below 5, as shown in FIG. 2, n=6, *p is less than 0.05, ***p is less than 0.001.

In the second animal group, compared with the blank control group, the rats in the model control group have erythema with more fine scales, and infiltrated hypertrophic skin lesions. Compared to the model control group, the erythema and the skin lesions of the rats in the anemoside B4 intragastric administration group (5 mg/kg), the anemoside B4 intragastric administration group (10 mg/kg), the anemoside B4 intragastric administration group (20 mg/kg), and the acitretin capsules (AC) intragastric administration group (8 mg/kg) are lightened. The results of PASI indicate that PASI of the model control group is significantly increased, and PASI of the anemoside B4 intragastric administration group (10 mg/kg), the anemoside B4 intragastric administration group (20 mg/kg), and the acitretin capsules (AC) intragastric administration group (8 mg/kg) are significantly decreased. As shown in FIG. 3, compared with the blank control group, $^{\#\#\#}$p is less than 0.001, and compared with the model control group, p is less than 0.01, and *p is less than 0.05, which indicate that anemoside B4 has a certain therapeutic effect on psoriasis lesions.

3.3. The Effect of Anemoside B4 on Serous M-CSF, VEGF, IL-6 and IL-17 Level

In the second animal group, compared with the blank control group, M-CSF, VEGF, IL-6 and IL-17 level in serum of the rats in the model control group is significantly increased, and M-CSF, VEGF, IL-6 and IL-17 level in serum of the rats in the anemoside B4 intragastric administration group (5 mg/kg), the anemoside B4 intragastric administration group (10 mg/kg), the anemoside B4 intragastric administration group (20 mg/kg), and the acitretin capsules (AC) intragastric administration group (8 mg/kg) is significantly decreased. As shown in FIG. 4, A refers to the M-CSF level, B refers to the VEGF level, C refers to the IL-6 level, and D refers to the IL-17 level. It is noted that $^{####}p$ is less than 0.001 compared to the blank control group, and *p is less than 0.01, and ***p is less than 0.05 compared to the model control group, which indicate that anemoside B4 may play the role of treating psoriasis by reducing the M-CSF, VEGF, IL-6 and IL-17 level in serum.

3.4. The Effect of Anemoside B4 on T Lymphocyte Subsets of $CD4^+$, $CD3^+$, $CD4^+/CD8^+$ In the second animal group, compared with the blank control group, the ratio of $CD4^+$, $CD3^+$, $CD4^+/CD8^+$ in serum of the rats in the model control group is significantly decreased, and the ratio of $CD4^+$, $CD3^+$, $CD4^+/CD8^+$ in serum of the rats in the anemoside B4 intragastric administration group (5 mg/kg), the anemoside B4 intragastric administration group (10 mg/kg), the anemoside B4 intragastric administration group (20 mg/kg), and the acitretin capsules (AC) intragastric administration group (8 mg/kg) is significantly increased. As shown in FIG. 5, A refers to the ratio of $CD4^+$, B refers to the ratio of $CD3^+$, and C refers to the ratio of $CD4^+/CD8^+$. It is noted that $^{####}p$ is less than 0.001 compared to the blank control group, and p is less than 0.01, and ***p is less than 0.05 compared to the model control group, which indicate that anemoside B4 may play the role of treating psoriasis by improving the $CD4^+$, $CD3^+$, $CD4^+/CD8^+$ level in serum.

3.5. The Effect of Anemoside B4 on the Spleen Coefficient and Immune Cells

Figure 6:
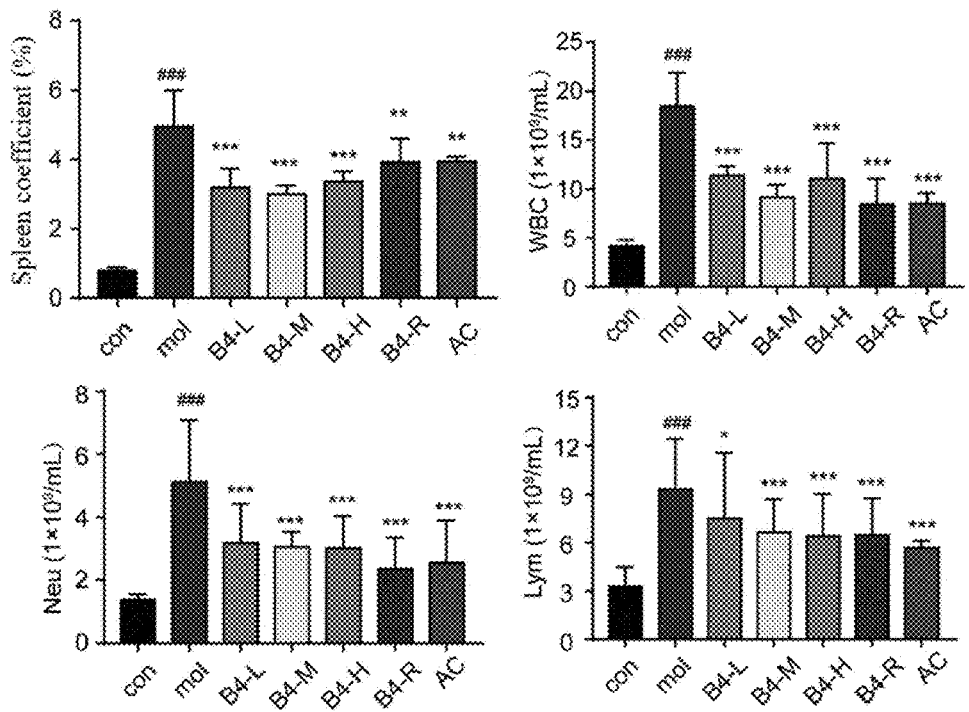
FIG. 6 is a diagram for showing the effect of anemoside B4 on the spleen coefficient and immune cells of the mice in the first animal group.

The spleen is an important immune organ, and the spleen coefficient can reflect the increase or decrease of immune cells in the spleen to a certain extent. In the first animal group, compared with the blank control group, the spleen of the mice in the model control group is significantly enlarged, the spleen coefficient is increased, and white blood cells (WBC), neutrophils (Neu) and lymphocyte (Lym) are increased. Compared with the model control group, the enlargement of the spleen of the mice in the anemoside B4 intragastric administration group (B4-L, 5 mg/kg), the anemoside B4 intragastric administration group (B4-M, 10 mg/kg), the anemoside B4 intragastric administration group (B4-H, 20 mg/kg), the acitretin capsules (AC) intragastric administration group (8 mg/kg), and the anemoside B4 cream group (B4-R, 20 mg/kg) is significantly relieved, the spleen coefficient is significantly decreased, and WBC, Neu and Lym are significantly decreased. As shown in FIG. 6, n=6, $^{####}p$ is less than 0.001, *p is less than 0.05, p is less than 0.01, and *p is less than 0.001.

3.6. The Effect of Anemoside B4 on IL-17, IL-12, IL-6 and IL-1β in Skin Tissue

Figure 7:
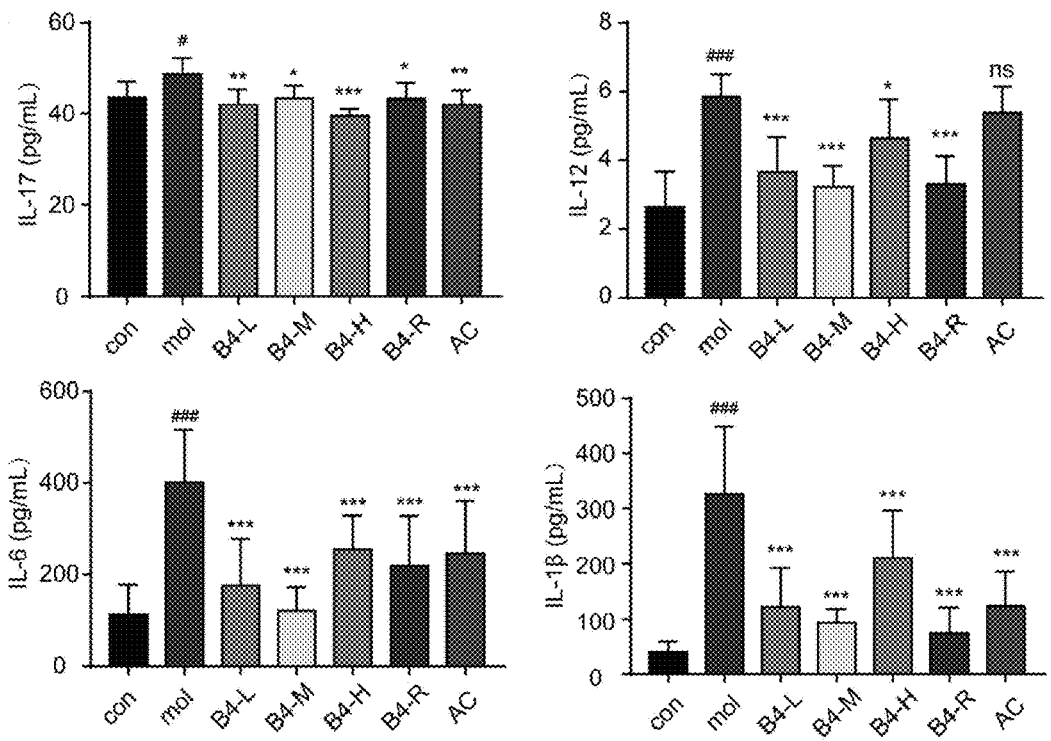
FIG. 7 is a diagram for showing the effect of anemoside B4 on IL-17, IL-12, IL-6 and IL-1β in skin tissue of the mice in the first animal group.

The release of cytokines of IL-17, IL-12, IL-6 and IL-1β in psoriasis-like lesions is increased. In the first animal group, compared with the blank control group, the level of IL-17, IL-12, IL-6 and IL-1β in the skin tissue of the mice in the model control group is significantly improved. Compared with the model control group, the level of IL-17, IL-12, IL-6 and IL-1β in the skin tissue of the mice in the anemoside B4 intragastric administration group (B4-L, 5 mg/kg), the anemoside B4 intragastric administration group (B4-M, 10 mg/kg), the anemoside B4 intragastric administration group (B4-H, 20 mg/kg), the acitretin capsules (AC) intragastric administration group (8 mg/kg), and the anemoside B4 cream group (B4-R, 20 mg/kg) is significantly reduced, wherein there are significant difference among the anemoside B4 intragastric administration group (5 mg/kg), the anemoside B4 intragastric administration group (10 mg/kg), the anemoside B4 intragastric administration group (20 mg/kg), and the anemoside B4 cream group (20 mg/kg). As shown in FIG. 7, n=6, $^{#}p$ is less than 0.05, $^{####}p$ is less than 0.001, *p is less than 0.05, p is less than 0.01, and *p is less than 0.001.

Figure 8:
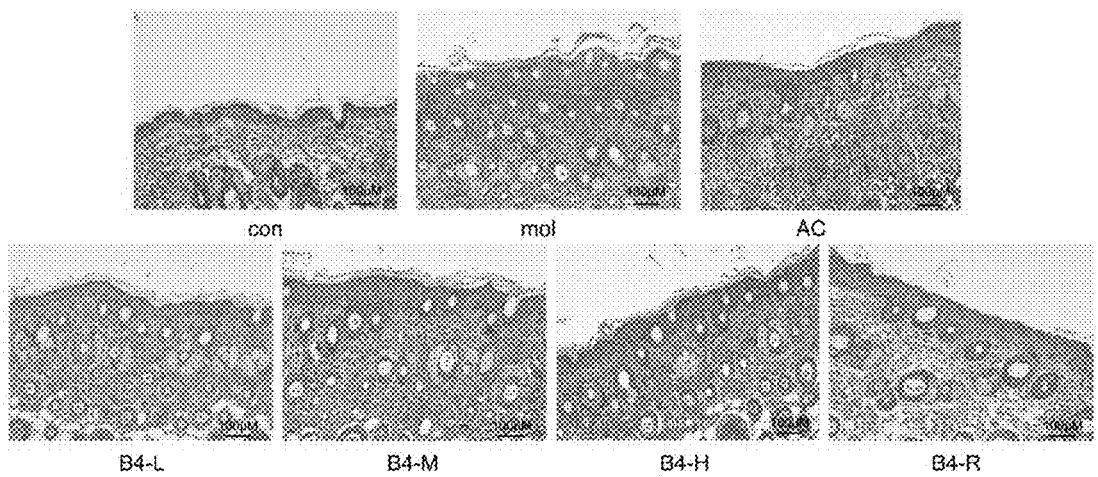
FIG. 8 is a diagram for showing the effect of anemoside B4 on skin pathological changes of the mice in the first animal group.

3.7. The Effect of Anemoside B4 on Skin Pathological Changes in the first animal group, as shown in FIG. 8, HE staining results of the skin tissue of the mice shows that, compared with the blank control group, the skin tissue of the mice in the 5% imiquimod-induced psoriasis model control group has the characteristics of inflammatory cell infiltration, acanthosis, thin or disappeared granular layer, parakeratosis or hyperkeratosis of stratum corneum, and telangiectasias in dermal layer. The psoriasis skin lesions of the mice in the anemoside B4 intragastric administration group (B4-L, 5 mg/kg), the anemoside B4 intragastric administration group (B4-M, 10 mg/kg), the anemoside B4 intragastric administration group (B4-H, 20 mg/kg), the acitretin capsules (AC) intragastric administration group (8 mg/kg), and the anemoside B4 cream group (B4-R, 20 mg/kg) are significantly improved.

4. Conclusion

Psoriasis as a chronic inflammatory skin disease has a long course and recurrence, and afflicts patients' physical and mental conditions. Currently, biological preparations are the most effective drugs for the treatment of psoriasis. However, adverse reactions will produce for long-term use. Therefore, it is urgent to find a safe and effective anti-psoriasis drug. The traditional Chinese medicine has the characteristics of many targets, wide components and less adverse reactions, and has certain advantages in the prevention and treatment of psoriasis. Anemoside B4 plays an active role in immune regulation and anti-inflammatory, but the therapeutic effect on psoriasis and possible mechanism have not been clarified.

IL-12 plays an important role in immune response and immune balance. During the occurrence of psoriasis, dendritic cells act on T cells by secreting IL-12 to make the T cells differentiate into T-helper cells such as Th1 and Th17, and then the secretion of cytokines such as IL-17 are increased. Research have showed that the IL-12 and IL-17 level increased significantly during the occurrence of psoriasis, and its expression level decreased significantly after drug treatment. In addition, IL-1β and IL-6 are also highly expressed in psoriatic lesions, which are produced by immune cells and keratinocytes, wherein the mechanism of IL-6 involved in psoriasis is that IL-6 can promote the secretion of Th17 cells and inhibit the production of Treg cells, resulting in the imbalance between the Th17 cells and the Treg cells. The expression of IL-1β during the occurrence of psoriasis is up-regulated, resulting in increasing the secretion of chemokines in keratinocytes and aggravating inflammation. Research have also showed that IL-1β can lead to the recurrence of psoriasis. During a process of psoriasis, IL-17 acts as an inflammatory transmitter to promote the production of IL-6 and IL-1β and causes severe inflammatory reaction, and IL-6 and IL-1β also promote the production of IL-17 and make the disease more and more serious. Compared with normal skin tissue, the level of IL-6 and IL-1β in the skin lesions of patients with psoriasis is significantly increased, which is positively correlated with the severity of psoriasis. Therefore, these cytokines are very important in the pathogenesis of psoriasis.

Anemoside B4 has a certain therapeutic effect on psoriasis. The experiment adopts psoriasis mice models induced by 5% imiquimod, the skin lesions and pathological changes of the psoriasis mice models are similar to human psoriasis, and it is recognized animal models for the study of psoriasis at home and abroad. The experimental results of the first animal group show that anemoside B4 can significantly improve the weight loss caused by psoriasis in the mice, lighten the skin lesions, reduce PASI, and reduce the damage of skin tissue, such as acanthosis, inflammatory cell infiltration, telangiectasias in dermal layer, hyperkeratosis of stratum corneum, etc., reduce the spleen coefficient and the number of immune cells in blood. The results show that anemoside B4 has an active therapeutic effect on the psoriasis mice models induced by 5% imiquimod. In the experiment, the improvement of the skin lesions and reversal of weight loss caused by imiquimod in anemoside B4 groups are better than those in the acitretin capsules (AC) intragastric administration group, which indicates that acitretin capsules have a certain efficacy, but has great side effects. Compared with the anemoside B4 intragastric administration groups, the anemoside B4 cream group has better effect, which indicates that transdermal administration is better than oral administration in the treatment of psoriasis, and can be further explored according to this result. Anemoside B4 can also significantly reduce the secretion of IL-12, IL-17, IL-6 and IL-1β in the skin tissue, which indicates that anemoside B4 may play the role of improving psoriasis skin lesions by inhibiting the release of IL-12, IL-17, IL-6 and IL-1β in the skin tissue.

The experimental results of the second animal group show that, compared with the blank control group, the rats in the model control group have erythema with more fine silver scales, and infiltrated hypertrophic skin lesions. The erythema and the skin lesions of the rats in anemoside B4 groups and the acitretin capsules (AC) intragastric administration group (8 mg/kg) are lightened, PASI of the model control group is increased, PASI of the anemoside B4 groups are decreased. The level of M-CSF, VEGF, IL-6 and IL-17 in the model control group is improved, and the level of M-CSF, VEGF, IL-6 and IL-17 in anemoside B4 groups is reduced. Compared with the blank control group, the ratio of $CD4^+$, $CD3^+$, $CD4^+/CD8^+$ in serum in the model control group is significantly decreased, and the ratio of $CD4^+$, $CD3^+$, $CD4^+/CD8^+$ in serum in anemoside B4 groups is significantly increased.

As a result, anemoside B4 has the therapeutic effect on 5% imiquimod-induced psoriatic lesions in mice. Its possible mechanism may be inhibiting inflammation reactions, regulating immune function and inhibiting angiogenesis, and the therapeutic effect may be realized by inhibiting the release of IL-12, IL-17, IL-6 and IL-1β in skin tissue. This study of the present disclosure laid a theoretical foundation for the subsequent development of anemoside B4 into an anti-psoriasis drug of traditional Chinese medicine.

The number of devices and processing scale described here are used to simplify the description of the utility. The application, modification and changes of the pilot-plant device for extraction of bone nutrient components of the utility will be obvious to those skilled in the art.

Although the embodiments of the present disclosure have been disclosed above, the present disclosure is not limited to the applications listed in the specification and the implementations. The present disclosure can be applied to various fields suitable for the present disclosure absolutely, and other modifications can be easily realized by those skilled in the art. Therefore, the present disclosure is not limited to the specific details and the illustrations shown and described herein without departing from the general concepts defined by the claims and equivalent scopes.

What is claimed is:

1. A method for treating psoriasis comprising a step of administering a therapeutic effective dosage of anemoside B4 with a structural formula (I) to a subject in need; wherein the therapeutic effective dosage of the anemoside B4 is 1-20 mg/kg per day;

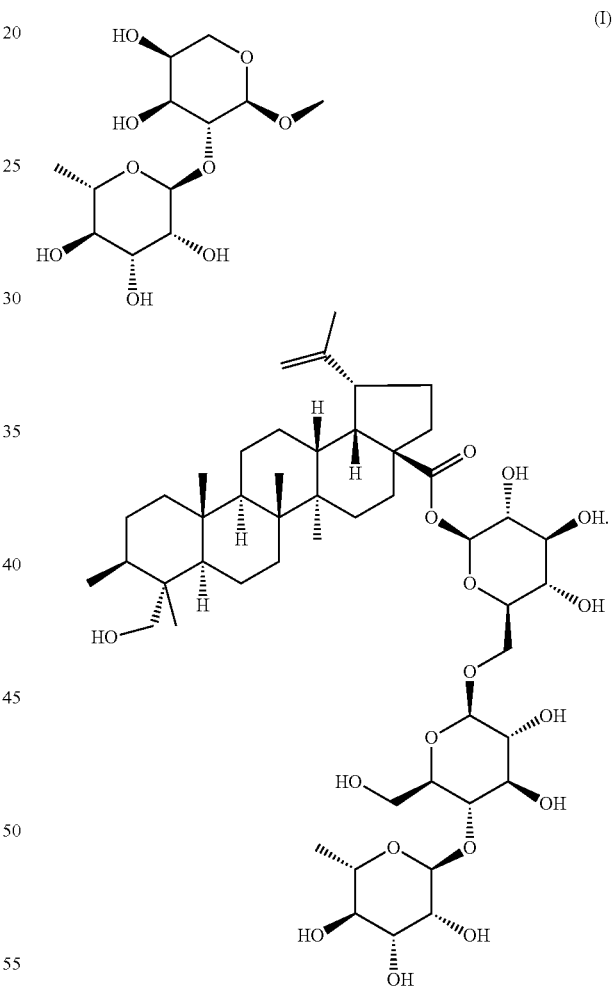

2. The method according to claim 1, wherein the anemoside B4 is prepared as a drug with a pharmaceutically acceptable carrier.

3. The method according to claim 2, wherein the drug further comprising hydrochloride, perchlorate, methanesulfonate, phosphate, citrate or sulfate of anemoside B4.

4. The method according to claim 2, wherein the pharmaceutically acceptable carrier is one or more selected from the group consisting of a diluent, a solubilizer, a cosolvent, a disintegrant, a dispersant, a lubricant, a corrective agent, an antioxidant, a binder, an absorbent, a wetting agent, a buffer and a crosslinking agent.

5. The method according to claim 2, wherein the drug is prepared as pills, tablets, powders, capsules, granules, dripping pills, drops, sprays, injections, suspensions, creams, gels or suppositories.

6. The method according to claim 5, wherein the creams are prepared by mixing stearic acid, glyceryl monostearate and castor oil, heating to 70-85° C. in a water bath, stirring to be completely melted to obtain an oil phase, mixing glycerin, the anemoside B4 and distilled water, heating to 70-85° C. in the water bath, adding triethanolamine under stirring until the anemoside B4 is completely dissolved to obtain a water phase, adding the oil phase into the water phase under continuous stirring, and clockwise stirring to 22-28° C.

* * * * *